US011006026B2

(12) United States Patent
Saito

(10) Patent No.: US 11,006,026 B2
(45) Date of Patent: May 11, 2021

(54) IMAGE CAPTURING APPARATUS

(71) Applicant: IKEGAMI TSUSHINKI CO., LTD., Tokyo (JP)

(72) Inventor: Takaaki Saito, Tokyo (JP)

(73) Assignee: IKEGAMI TSUSHINKI CO., LTD., Tokyo (JP)

(*) Notice: Subject to any disclaimer, the term of this patent is extended or adjusted under 35 U.S.C. 154(b) by 0 days.

(21) Appl. No.: 16/641,089

(22) PCT Filed: Jul. 11, 2018

(86) PCT No.: PCT/JP2018/026176
§ 371 (c)(1),
(2) Date: Feb. 21, 2020

(87) PCT Pub. No.: WO2019/044193
PCT Pub. Date: Mar. 7, 2019

(65) Prior Publication Data
US 2020/0195819 A1 Jun. 18, 2020

(30) Foreign Application Priority Data
Sep. 4, 2017 (JP) .............................. JP2017-169153

(51) Int. Cl.
*H04N 5/225* (2006.01)
*H04N 9/04* (2006.01)
(Continued)

(52) U.S. Cl.
CPC ....... *H04N 5/2254* (2013.01); *H04N 5/23293* (2013.01); *H04N 5/332* (2013.01); *H04N 9/0455* (2018.08); *H04N 9/04553* (2018.08)

(58) Field of Classification Search
CPC .. H04N 5/2254; H04N 9/04553; H04N 5/332; H04N 9/0455; H04N 5/23293; A61B 1/00; G02B 23/24
See application file for complete search history.

(56) References Cited

U.S. PATENT DOCUMENTS 5,749,830 A    5/1998   Kaneko et al.
6,330,055 B1 * 12/2001   Higashino ................ G02B 7/32
                                                                    356/3.06
(Continued)

FOREIGN PATENT DOCUMENTS

JP      H7-155292 A    6/1995
JP      2009-95683 A    5/2009
(Continued)

OTHER PUBLICATIONS

International Search Report issued in PCT/JP2018/026176 dated Oct. 9, 2018 with English Translation (5 pages).

*Primary Examiner* — Timothy J Henn
(74) *Attorney, Agent, or Firm* — Nakanishi IP Associates, LLC

(57) ABSTRACT

Provided is an image capturing apparatus that not only prevents excitation light from leaking into RGB but also corrects a difference of focal points between visible light and IR and corrects levels of visible light and IR without having a complicated structure. An image capturing apparatus 10 includes a light irradiation unit 12 that irradiates an object including a fluorescent material with excitation light and illuminating light, a four-color separation unit 16 that separates light incident upon a lens 14 into R, G, B, and IR, an image sensor 18 that performs photoelectric conversion on each separated light, a picture signal output unit 20 that generates a picture signal from an electrical signal obtained by the photoelectric conversion, a picture display 22 that displays a picture based on the picture signal, a bandpass filter 24 that does not transmit light near a wavelength band of the excitation light, and a correction filter 26. The correction filter 26 includes a circular visible light cutting region 30 that cuts visible light out of the incident light, a circular IR cutting region 28 that cuts IR out of the incident (Continued)

light, and a dummy glass 32 having a predetermined thickness.

2 Claims, 4 Drawing Sheets

(51) Int. Cl.
*H04N 5/232* (2006.01)
*H04N 5/33* (2006.01)

(56) References Cited

U.S. PATENT DOCUMENTS

| | | |
|---|---|---|
| 2007/0016077 A1 | 1/2007 | Nakaoka et al. |
| 2016/0286187 A1 | 9/2016 | Takenaga et al. |
| 2017/0111557 A1* | 4/2017 | Ko .................... G02B 5/26 |
| 2017/0339377 A1* | 11/2017 | Hashimoto .......... A61B 5/0086 |
| 2019/0235236 A1* | 8/2019 | Ollila ................ G02B 27/0093 |
| 2020/0163538 A1* | 5/2020 | Takahashi .......... A61B 1/00045 |

FOREIGN PATENT DOCUMENTS

| | | |
|---|---|---|
| JP | 2016-87062 A | 5/2016 |
| JP | 2016-178995 A | 10/2016 |
| JP | 6025130 B2 | 11/2016 |
| JP | 2017-053890 A | 3/2017 |

\* cited by examiner

CHARACTERISTICS OF FOUR-COLOR SEPARATION PRISM

TOTAL SPECTRAL CHARACTERISTICS

IMAGE CAPTURING APPARATUS

TECHNICAL FIELD

The present invention relates to an image capturing apparatus that takes a picture of an object including a fluorescent material and displays the picture. Particularly, the present invention relates to an image capturing apparatus that corrects a difference of focal points between incident visible light (R/G/B) and IR and also corrects levels of visible light and IR.

BACKGROUND ART

In the related art, there are known an image capturing apparatus including a four-color separation prism and an imaging system including an endoscope. In other words, when taking a picture, those known technique employs a separation prism that separates light incident upon a lens into R/G/B components and an IR component.

For example, Patent Literature 1 discloses an endoscope including a four-color separation prism provided with a blue color separation prism, a red color separation prism, a green color separation prism, and an IR separation prism. The blue color separation prism, the red color separation prism, and the green color separation prism separate light from an affected area into a blue component, a red component, and a green component, respectively. The IR separation prism separates light from the affected area into an IR component. The endoscope disclosed in Patent Literature 1 also includes a blue image sensor that is installed in the blue color separation prism and converts the separated blue component into an electrical signal, a red image sensor that is installed in the red color separation prism and converts the separated red component into an electrical signal, a green image sensor that is installed in the green color separation prism and converts the separated green component into an electrical signal, an IR image sensor that is installed in the IR separation prism and converts the separated IR component into an electrical signal, and a signal output unit that outputs an RGB signal and an IR signal from each converted electrical signal. The IR separation prism is placed closer to an object than the blue color separation prism, the red color separation prism, and the green color separation prism with respect to incident light from the affected area, and the IR separation prism transmits light of the blue component, the red component, and the green component.

Patent Literature 2 discloses an image capturing apparatus provided with a color separation prism including a dichroic film that separates light within the visible-light wavelength band and light within the emitted-light wavelength band, a fluorescence image capturing device that is disposed at the back of the color separation prism and forms an image with light within the emitted-light wavelength band separated by the dichroic film, a visible light image capturing device that is disposed at the back of the color separation prism and forms an image with light within the visible-light wavelength band separated by the dichroic film, a bandpass filter that is disposed between the color separation prism and the fluorescence image capturing device and has an incident surface perpendicular to an optical axis. In this image capturing apparatus, the fluorescence image capturing device and the visible light image capturing device are arranged in such a manner that a difference in length between a light path for emitted light that forms an image in the fluorescence image capturing device through the color separation prism and a light path for visible light that forms an image in the visible light image capturing device through the color separation prism corresponds to a shift between a position of fluorescence image and a position of visible light image caused by an imaging lens mounted in front of the color separation prism.

Furthermore, in this image capturing apparatus, the fluorescence image capturing device and the visible light image capturing device are fixed or arranged to make a distance between the devices variable so as to correspond to the difference in length of the light paths. With such a structure, the image capturing apparatus adjusts a difference of focal points between RGB within the visible-light wavelength band and IR within the emitted-light wavelength band.

CITATION LIST

Patent Literature

Patent Literature 1: JP 6025130 B2
Patent Literature 2: JP 2017-53890 A

SUMMARY OF INVENTION

Technical Problem

Although the technique disclosed in Patent Literature 1 is expected to be applied to image capturing using indocyanine green (hereinafter referred to as ICG) as a fluorescent material, Patent Literature 1 does not mention spectral characteristics. Furthermore, excitation light such as ICG has a wavelength of 750 nm to 810 nm, but light having characteristics illustrated in a figure of the disclosed technique is sensed even at 800 nm or less. Accordingly, excitation light leaks into RGB components, which may cause a problem in composite images.

Generally, RGB and IR have focuses deviated from each other due to different focal positions. In the technique disclosed in Patent Literature 1, it is required to correct the focal positions by bonding each sensor to a lens system to be used. This technique leads to a complicated structure. Since IR sensitivity which is important in such technology is improved by adding peripheral pixels, it is difficult to obtain desired sensitivity.

In addition, as described above, the technique disclosed in Patent Literature 2 corresponds to a difference of focal points between RGB and IR, having a structure in which the fluorescence image capturing device and the visible light image capturing device are fixed or arranged to make a distance between the devices variable so as to correspond to the difference in length of the light paths. This technique also leads to a complicated structure.

The present invention has been made to solve the problems, and an object of the present invention is to provide an image capturing apparatus that not only prevents excitation light such as ICG from leaking into RGB but also corrects a difference of focal points between visible light and IR and corrects levels of visible light and IR without having a complicated structure as a whole.

Solution to Problem

According to an embodiment of the present invention, there is provided an image capturing apparatus including: a light irradiation unit that irradiates an object including a fluorescent material with excitation light that excites the fluorescent material and with light that illuminates the object; a four-color separation unit that separates light incident from the object upon a mounted lens into an R component, a G component, a B component, and an IR component; an image sensor that receives each incident light separated by the four-color separation unit and performs photoelectric conversion on each incident light; a picture signal output unit that generates and outputs a picture signal from an electrical signal obtained by the photoelectric conversion by the image sensor; a picture display that displays a picture based on the picture signal output by the picture signal output unit; a bandpass filter that is interposed between the mounted lens and the four-color separation unit and does not transmit light near a wavelength band of the excitation light; and a correction filter interposed between the bandpass filter and the mounted lens, wherein the correction filter includes a visible light cutting region having a circular shape, an IR cutting region having a circular shape and disposed at a central position of the visible light cutting region, and a dummy glass disposed on a surface of the IR cutting region facing the bandpass filter, wherein the visible light cutting region cuts visible light out of the incident light, the IR cutting region cuts IR out of the incident light, and the dummy glass has a circular shape corresponding to the circular shape of the IR cutting region and has a predetermined thickness.

According to an embodiment of the present invention, since the correction filter is mounted at a focusing position of an optical system (such as the lens and a microscope adapter) attached to the image capturing apparatus, visible light is focused, which increases a depth of field. Furthermore, the IR cutting on the side of visible light and the thickness of the dummy glass enables correction of a difference of focal points between visible light and IR. In addition, since visible light is focused, the level of visible light is reduced, and consequently, it is possible to accurately correct levels of visible light and IR entering the optical system.

The correction filter is preferably provided with a dummy glass having a thickness according to the IR.

DESCRIPTION OF EMBODIMENTS

Figure 1B:
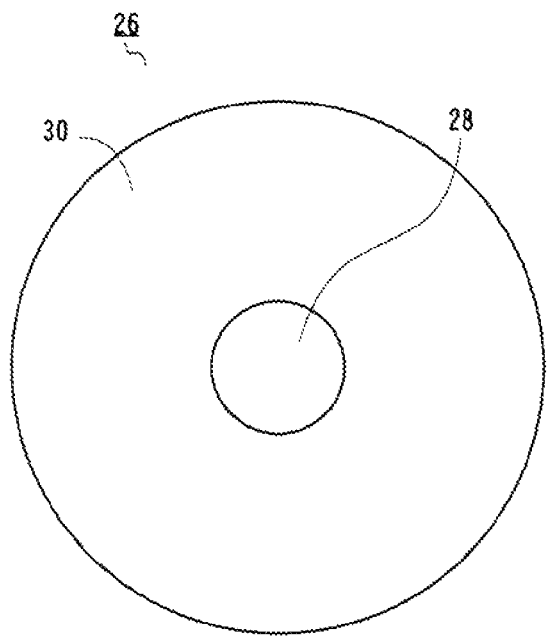
FIG. 1(a) is a side view and FIG. 1(b) is a front view each illustrating a structure of a correction filter of an image capturing apparatus according to an embodiment of the present invention.
Figure 1A:
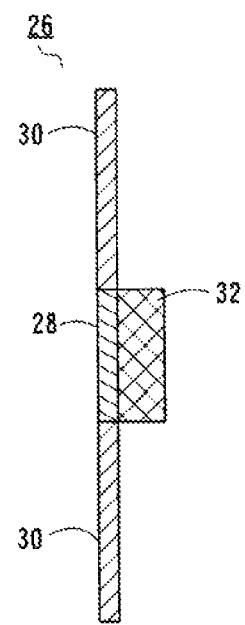
Figure 2:
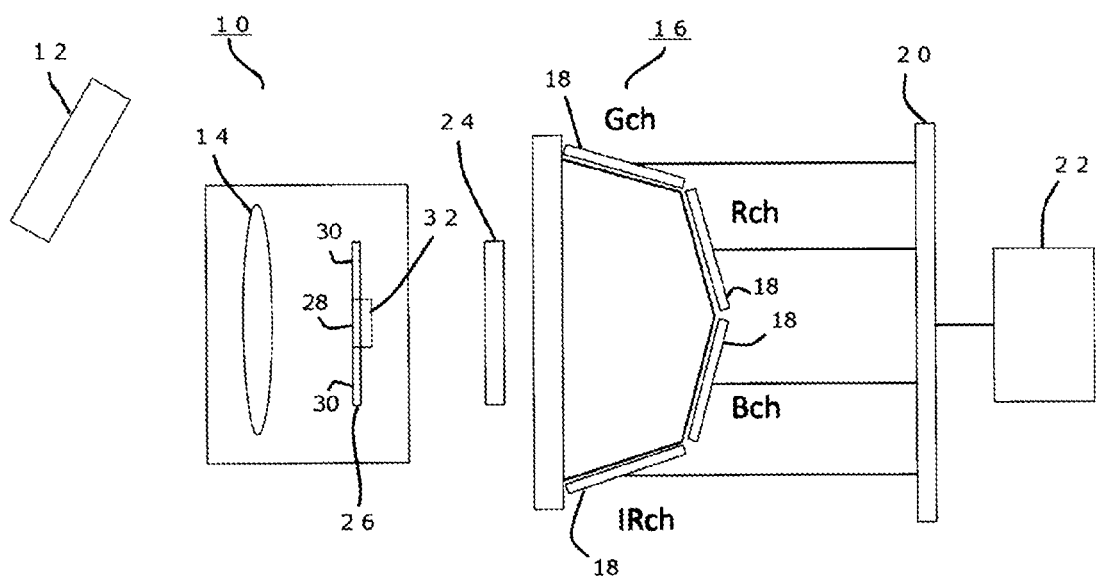
FIG. 2 is a schematic view illustrating a configuration of the image capturing apparatus according to the embodiment of the present invention.

An image capturing apparatus according to an embodiment of the present invention will be described with reference to the drawings. FIG. 1(a) is a side view and FIG. 1(b) is a front view each illustrating a structure of a correction filter of an image capturing apparatus according to an embodiment of the present invention. FIG. 2 is a schematic view illustrating a configuration of the image capturing apparatus according to the embodiment of the present invention.

In regard to reference numerals, 10 denotes an image capturing apparatus, 12 denotes a light irradiation unit, 14 denotes a lens, 16 denotes a four-color separation unit, 18 denotes an image sensor, 20 denotes a picture signal output unit, 22 denotes a picture display, 24 denotes a bandpass filter, 26 denotes a correction filter, 28 denotes an IR cutting region, 30 denotes a visible light cutting region, and 32 denotes a dummy glass.

As illustrated in FIG. 2, the image capturing apparatus 10 according to this embodiment includes the light irradiation unit 12 and the four-color separation unit 16. The light irradiation unit 12 irradiates an object including a fluorescent material with excitation light that excites the fluorescent material and with light that illuminates the object. The four-color separation unit 16 separates light incident from the object upon the mounted lens 14 into an R component, a G component, a B component, and an IR component.

The image capturing apparatus 10 also includes the image sensor 18, the picture signal output unit 20, the picture display 22, the bandpass filter 24, and the correction filter 26. The image sensor 18 receives each incident light separated by the four-color separation unit 16 and performs photoelectric conversion on each incident light. The picture signal output unit 20 generates and outputs a picture signal from an electrical signal obtained by the photoelectric conversion by the image sensor 18. The picture display 22 displays a picture based on the picture signal output by the picture signal output unit 20. The bandpass filter 24 is interposed between the lens 14 and the four-color separation unit 16 and does not transmit light near a wavelength band of the excitation light. The correction filter 26 is interposed between the bandpass filter 24 and the lens 14.

In this embodiment, the correction filter 26 includes the visible light cutting region 30, the IR cutting region 28 disposed at a central position of the visible light cutting region 30, and the dummy glass 32 disposed on a surface of the IR cutting region 28 facing the bandpass filter 24. The visible light cutting region 30 cuts visible light out of the incident light. The IR cutting region 28 that has a circular shape cuts IR out of the incident light. The dummy glass 32 has a circular shape corresponding to the circular shape of the IR cutting region 28 and has a predetermined thickness.

Next, the image capturing apparatus according to an embodiment of the present invention will be described in more detail. In surgeries using an image capturing apparatus including an endoscope and the like, the following technique is employed. That is, a fluorescent material such as indocyanine green (ICG) is administered to a body, and an affected area with aggregate ICG is irradiated with near infrared rays so as to capture an image of a site including the affected area.

In a case where an image of an affected area is captured by receiving light including IR with a single-plate image capturing apparatus that includes one image sensor, it is required to dispose filters for R, G, B, and IR separated into quarters on an incident surface of the image sensor. Accordingly, the image sensor increases in size, which makes it difficult to use the image sensor in an image capturing apparatus including an endoscope and the like.

The image capturing apparatus according to this embodiment is provided with the four-color separation unit 16 that separates light incident from an object upon the mounted lens 14 into an R component, a G component, a B component, and an IR component so as to prevent each image sensor from increasing in size. Accordingly, it is possible to downsize the apparatus as a whole and to enable application to an image capturing apparatus including an endoscope and the like.

Suppose that white light is used to capture an image with an image capturing apparatus including a microscope. In this case, the captured image includes a fluorescence image. However, since white light (including excitation light) is background light, the fluorescence image shows no contrast at all. If an image is captured in a similar manner, using illuminating light that includes only excitation light and optimum sharp cut filters disposed on the side of the excitation light and on an image capturing color filter, the captured image will be a fluorescence image showing excellent contrast which is overwhelmingly different from the contrast in the image using white light.

As described above, in order to obtain a high-quality fluorescence image with good contrast, it is required to cut the excitation light in the background light. Accordingly, in this embodiment, the bandpass filter 24 that has a plurality of transmittance values and does not transmit light near a wavelength band of the excitation light is interposed between the lens 14 and the four-color separation unit 16.

Figure 3:
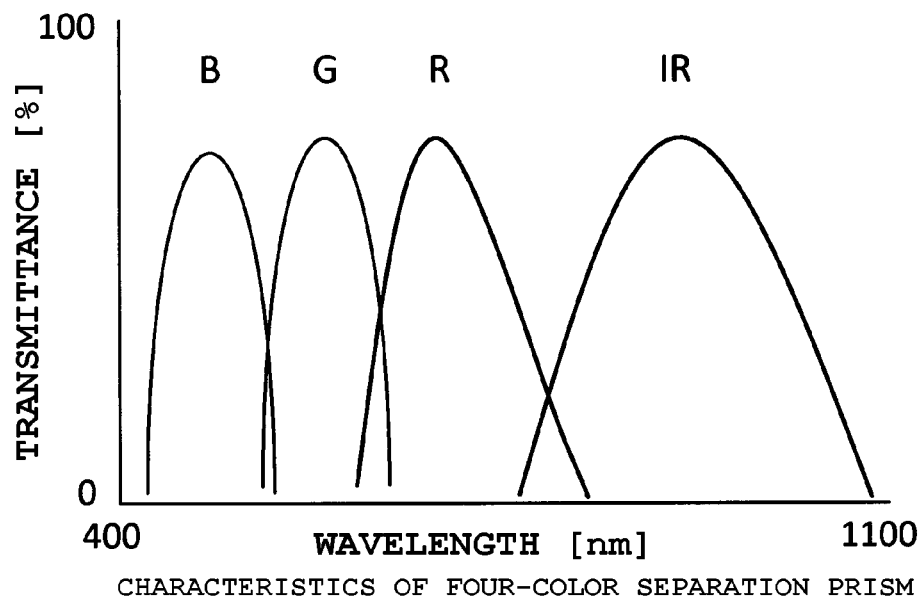
FIG. 3 is a graph illustrating spectral characteristics of a four-color separation prism.
Figure 4:
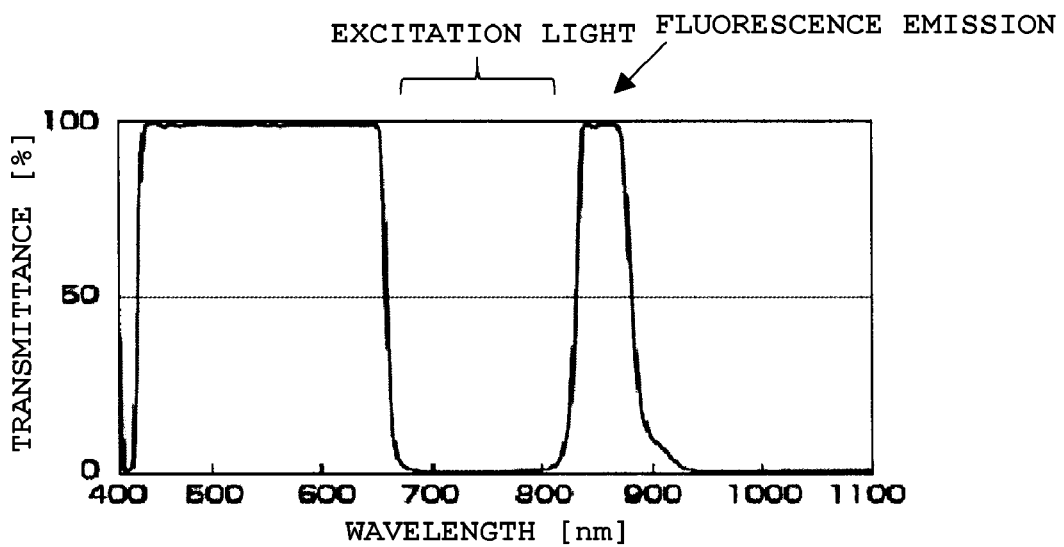
FIG. 4 is a graph illustrating characteristics of an optical bandpass filter.
Figure 5:
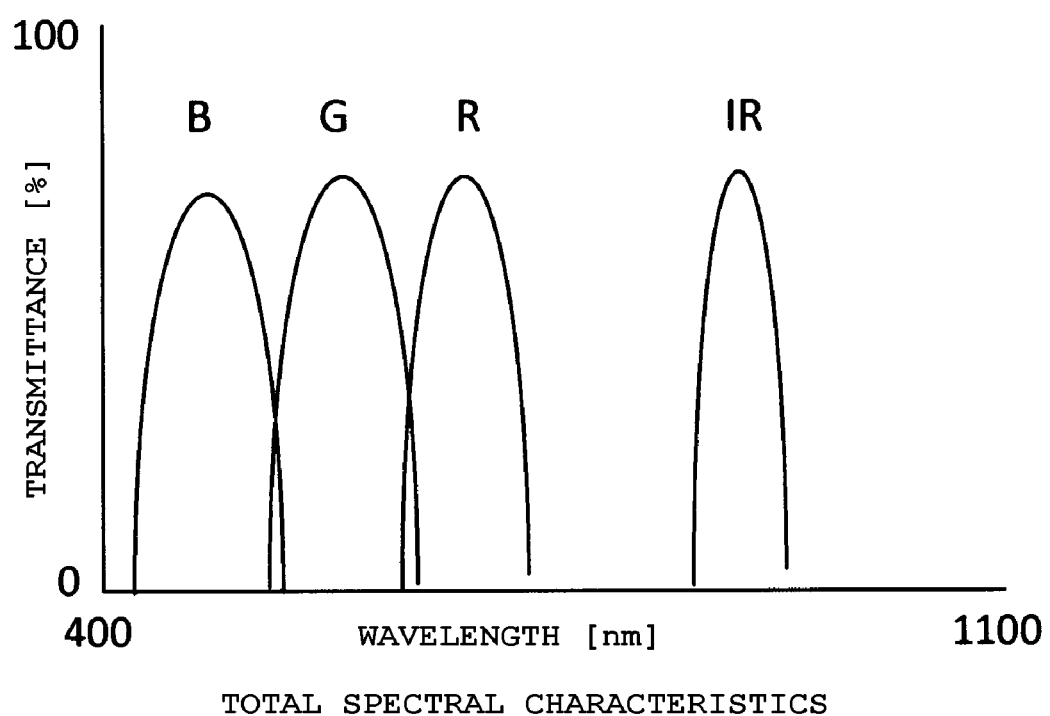
FIG. 5 is a graph illustrating spectral characteristics (total spectral characteristics) when the four-color separation prism and the optical bandpass filter are combined.

In other words, as in characteristics of an optical bandpass filter illustrated in FIG. 4, it is possible to cut the excitation light in the background light by a bandpass filter having extremely low transmittance with respect to the wavelength band of the excitation light. With this bandpass filter 24, spectral characteristics of a four-color separation prism illustrated in FIG. 3 changes to spectral characteristics illustrated in FIG. 5 (four-color separation prism+bandpass filter). Note that the bandpass filter 24 is exchangeable and used for a plurality of fluorescence observations by changing filters.

In a fluorescence microscope, a module with a set of filters for excitation light and imaging color is exchanged according to a fluorescent dye to be used. However, in an image capturing apparatus such as a camera, it is difficult to exchange four-plate prisms. Therefore, cut-off characteristics of filters for excitation light and imaging color are standardized according to a fluorescent dye and a fluorescent probe to be used, which makes it easy to change the characteristics with an optical filter.

In this embodiment, the correction filter 26 is interposed between the bandpass filter 24 and the lens 14. As illustrated in FIG. 1(*b*), the correction filter 26 includes the visible light cutting region 30 that cuts visible light out of the incident light, and includes the circular IR cutting region 28 that is disposed at a central position of the visible light cutting region 30 and cuts IR out of the incident light.

With such a configuration, when visible light from the object illuminated by the light irradiation unit 12 enters the lens 14 of the image capturing apparatus 10, the IR cutting region 28 focuses the visible light, leading to an increase in depth of field.

As illustrated in FIG. 1(*a*), the surface of the IR cutting region 28 facing the bandpass filter 24 is provided with the dummy glass 32 that has a circular shape corresponding to the circular shape of the IR cutting region 28 and has a predetermined thickness. This dummy glass 32 shifts focal positions of visible light so as to match focal positions of visible light and IR.

With such a structure, the apparatus herein enables correction of focal positions of visible light and IR without complicated equipment or structure. Note that the apparatus selectively employs the correction filter 26 provided with the dummy glass 32 having a thickness according to IR (corresponding to a wavelength of IR). Accordingly, it is possible to correct a difference of focal points between visible light and IR from any type of fluorescent materials.

INDUSTRIAL APPLICABILITY

An image capturing apparatus according to an embodiment of the present invention not only prevents excitation light such as ICG from leaking into RGB but also corrects a difference of focal points between visible light and IR and corrects levels of visible light and IR without having a complicated structure as a whole.

REFERENCE SIGNS LIST

10 Image capturing apparatus
12 Light irradiation unit
14 Lens
16 Four-color separation unit
18 sensor
20 signal output unit
22 Picture display
24 Bandpass filter
26 Correction filter
28 IR cutting region
30 Visible light cutting region
32 Dummy glass

The invention claimed is:
1. An image capturing apparatus comprising:
 a light irradiator that irradiates an object including a fluorescent material with excitation light that excites the fluorescent material and with light that illuminates the object;
 a four-color separator that separates light incident from the object upon a mounted lens into an R component, a G component, a B component, and an IR component;
 an image sensor that receives each incident light separated by the four-color separator and performs photoelectric conversion on each incident light;
 a picture signal generator that generates and outputs a picture signal from an electrical signal obtained by the photoelectric conversion by the image sensor;
 a picture display that displays a picture based on the picture signal output by the picture signal generator;
 a bandpass filter that is interposed between the mounted lens and the four-color separator and does not transmit light near a wavelength band of the excitation light; and
 a correction filter interposed between the bandpass filter and the mounted lens,
 wherein the correction filter includes a visible light cutting region having a circular shape, an IR cutting region having a circular shape and disposed at a central position of the visible light cutting region, and a dummy glass disposed on a surface of the IR cutting region facing the bandpass filter,
 wherein the visible light cutting region cuts visible light out of the incident light, the IR cutting region cuts IR out of the incident light, and the dummy glass has a circular shape corresponding to the circular shape of the IR cutting region and has a predetermined thickness.
2. The image capturing apparatus according to claim 1, wherein the correction filter is provided with a dummy glass having a thickness according to a wavelength of the IR component of the incident light.

* * * * *